(12) United States Patent
Kobayashi et al.

(10) Patent No.: US 8,034,732 B2
(45) Date of Patent: Oct. 11, 2011

(54) ANTIMICROBIAL GLASS AND METHOD OF PRODUCING ANTIMICROBIAL GLASS

(75) Inventors: Yoshinao Kobayashi, Tokyo (JP); Mamoru Kitamura, Tokyo (JP); Shinobu Kanamaru, Tokyo (JP); Kenichi Tanaka, Tokyo (JP)

(73) Assignee: Koa Glass Co., Ltd., Edogawa-Ku, Tokyo (JP)

( * ) Notice: Subject to any disclaimer, the term of this patent is extended or adjusted under 35 U.S.C. 154(b) by 318 days.

(21) Appl. No.: 12/224,487

(22) PCT Filed: Feb. 2, 2007

(86) PCT No.: PCT/JP2007/052302
§ 371 (c)(1),
(2), (4) Date: Aug. 28, 2008

(87) PCT Pub. No.: WO2007/108245
PCT Pub. Date: Sep. 27, 2007

(65) Prior Publication Data
US 2010/0004111 A1     Jan. 7, 2010

(30) Foreign Application Priority Data
Mar. 17, 2006 (JP) .................. 2006-074641

(51) Int. Cl.
*C03C 3/087* (2006.01)
*C03C 3/16* (2006.01)
*A01N 59/16* (2006.01)
*A61K 33/24* (2006.01)
*A61K 33/38* (2006.01)

(52) U.S. Cl. ............. 501/71; 501/45; 424/617; 424/618

(58) Field of Classification Search .............. 501/45–48, 501/64, 71, 78; 424/617, 618
See application file for complete search history.

(56) References Cited

U.S. PATENT DOCUMENTS

| | | | |
|---|---|---|---|
| 6,831,028 B1 * | 12/2004 | Ishii et al. | 501/33 |
| 2003/0157176 A1 * | 8/2003 | Nakamura et al. | 424/486 |
| 2005/0069592 A1 * | 3/2005 | Fechner et al. | 424/604 |
| 2005/0095303 A1 * | 5/2005 | Krenitski et al. | 424/604 |
| 2005/0233888 A1 * | 10/2005 | Seneschal et al. | 501/45 |
| 2006/0166806 A1 * | 7/2006 | Fechner et al. | 501/45 |
| 2006/0172877 A1 | 8/2006 | Fechner et al. | |

FOREIGN PATENT DOCUMENTS

| | | |
|---|---|---|
| JP | H01-313531 | 12/1989 |
| JP | H07-025635 | 1/1995 |
| JP | U H07-063701 | 7/1995 |

(Continued)

*Primary Examiner* — Jerry A Lorengo
*Assistant Examiner* — Noah Wiese
(74) *Attorney, Agent, or Firm* — Manabu Kanesaka

(57) ABSTRACT

An antimicrobial glass is provided which can release a predetermined amount of silver ion rapidly for a long period of time and can provide a predetermined antimicrobial treatment repeatedly to a matter to be antibacterialized during or after washing and which is excellent in discoloration prevention effect and discriminativity, and a method for producing the same is also provided.

A tabular antimicrobial glass capable of exerting an antimicrobial effect by releasing silver ions, wherein the maximum diameter (t1) is adjusted within the range of 3 to 30 mm and which contains an inorganic coloring agent as a compounded component, wherein the addition amount of the inorganic coloring agent is adjusted to a value within the range of 0.001 to 0.5% by weight to the total amount.

4 Claims, 12 Drawing Sheets

FOREIGN PATENT DOCUMENTS

| | | |
|---|---|---|
| JP | H10-072530 | 3/1998 |
| JP | H11-319042 | 11/1999 |
| JP | 2002-003238 | 1/2002 |
| JP | 2002-003239 | 1/2002 |
| JP | 2002-343261 | 11/2002 |
| JP | 2005-162519 | 6/2005 |
| KR | 1020060012326 A * | 2/2006 |
| WO | WO-2005-087675 A1 * | 9/2005 |
| WO | WO 2005/087675 A1 | 9/2005 |

* cited by examiner

Addition amount of inorganic coloring agent (% by weight)

Fig.6
(a)
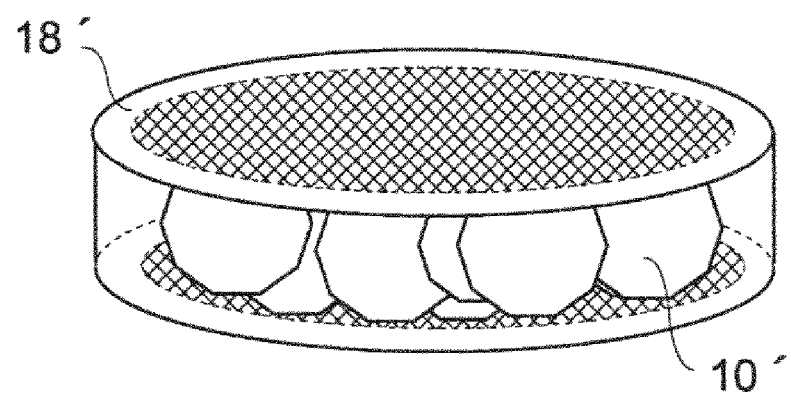
(b)
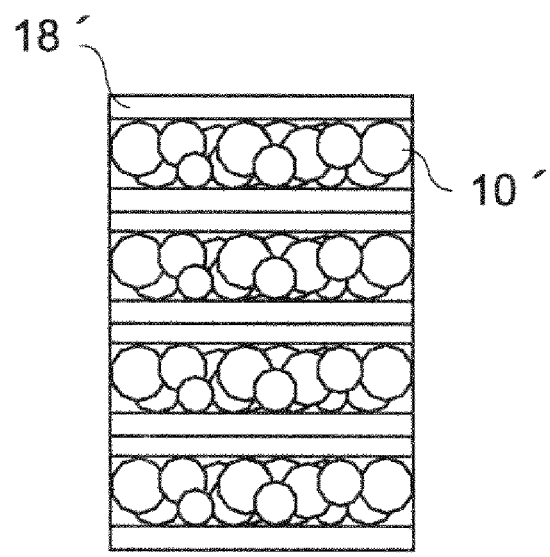

Fig.7
(a)
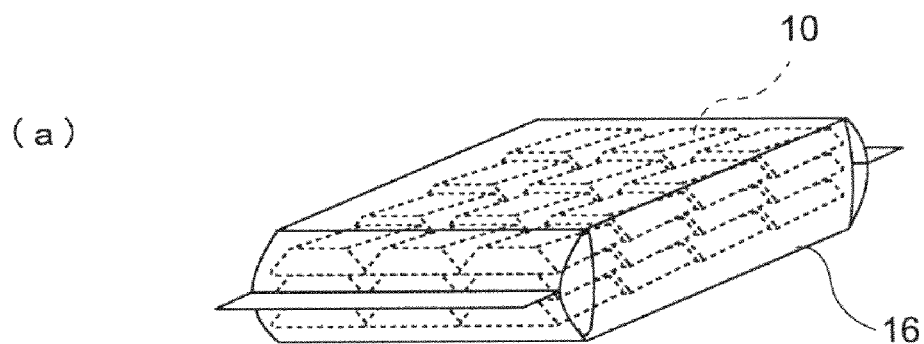
(b)
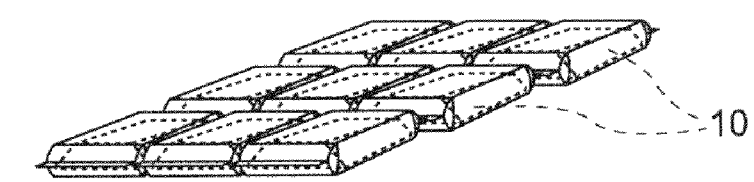
(c)
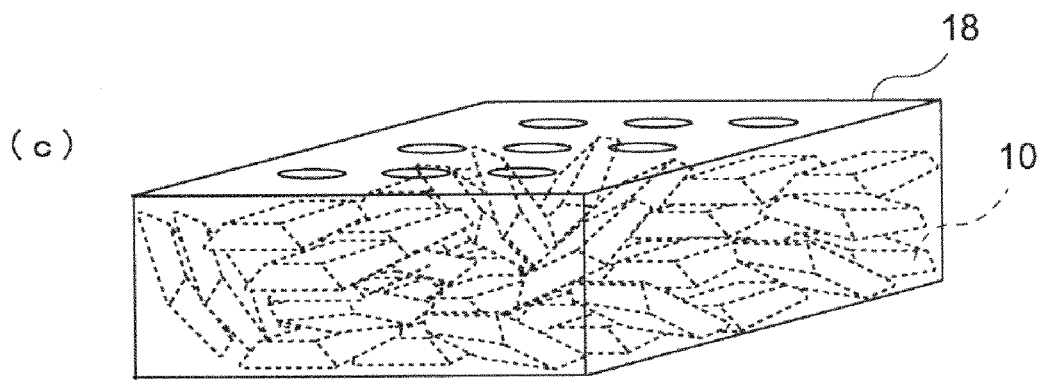

Fig.9
(a)
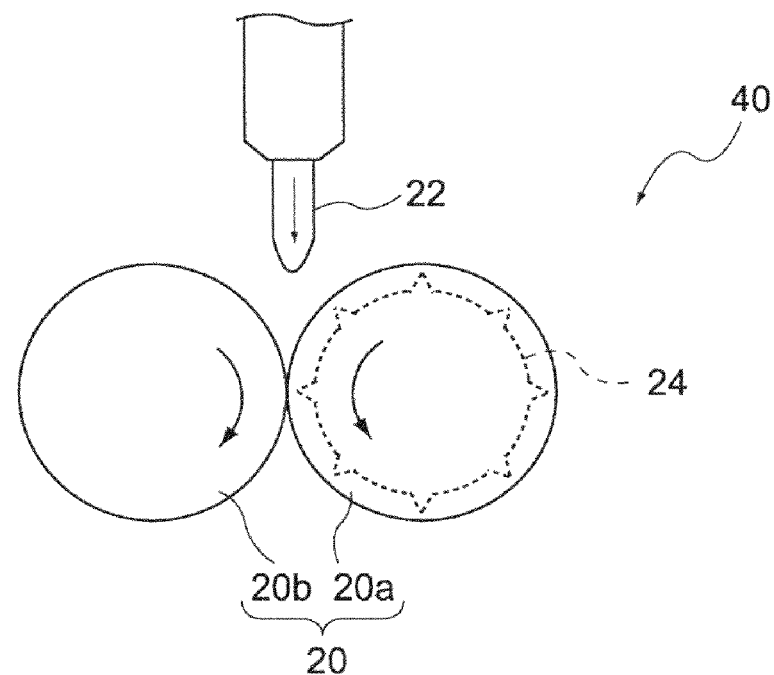
(b)
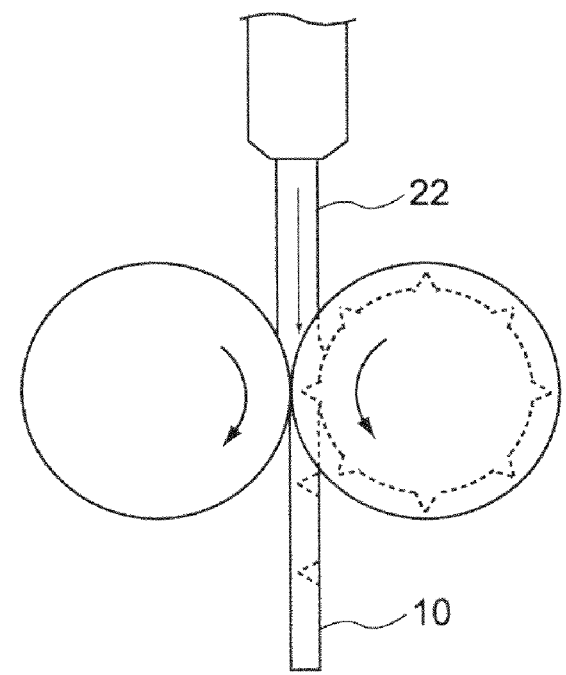

Fig.12
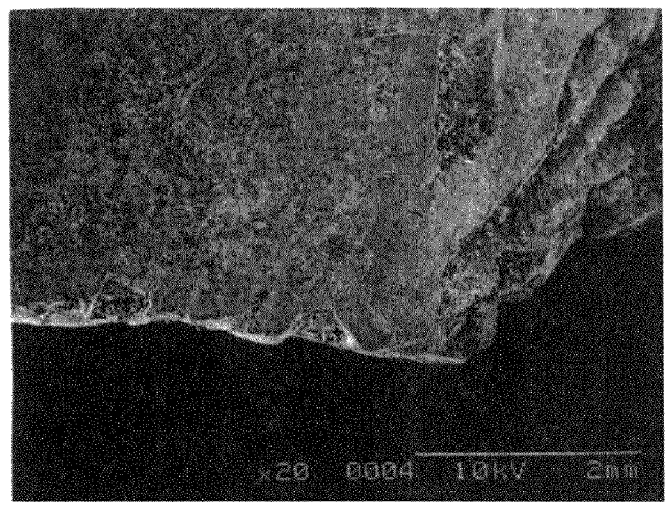
(a) No flash removing
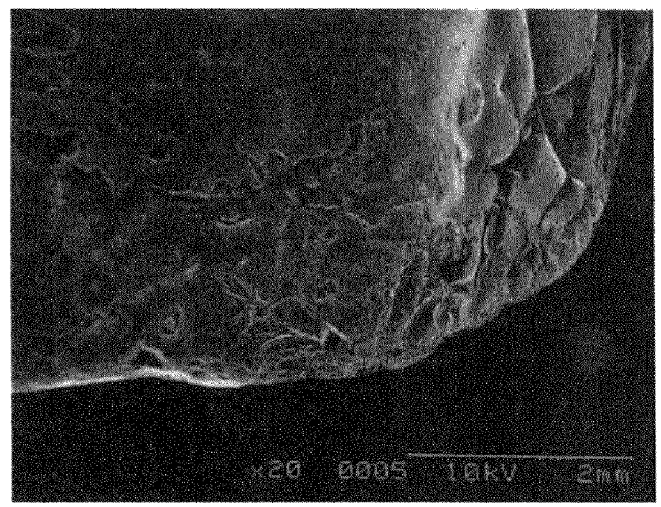
(b) Flash removing for 1 hour
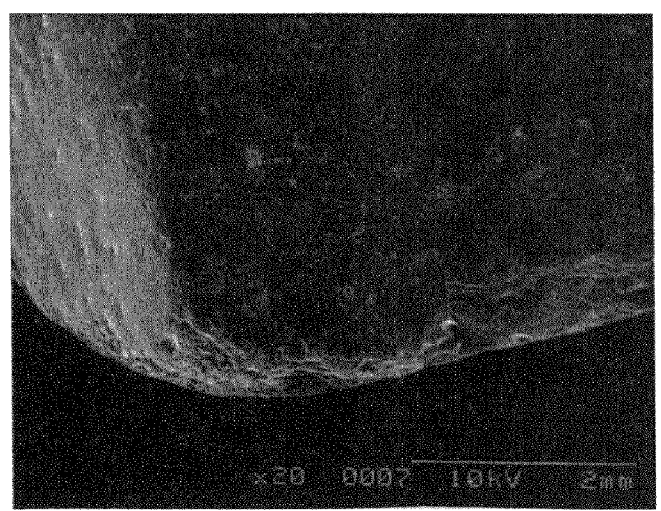
(c) Flash removing for 3 hours

ANTIMICROBIAL GLASS AND METHOD OF PRODUCING ANTIMICROBIAL GLASS

BACKGROUND OF THE INVENTION

1. Field of the Invention

The present invention relates to antimicrobial glass and methods for producing antimicrobial glass, and particularly to antimicrobial glass excellent in discoloration prevention effect and in discriminativity which contains an inorganic coloring agent, and to methods for producing antimicrobial glass.

2. Description of the Related Art

Recently, in the field of construction materials, home electric appliances (including television sets, personal computers, mobile telephones and video cameras), sundries, packaging materials, etc., there have been used antimicrobial resin compositions produced by mixing a predetermined amount of antimicrobial glass having a predetermined particle size into resin in order to impart an antimicrobial effect.

As such an antimicrobial resin composition, a synthetic resin molded body which contains, in the resin, a borosilicate antimicrobial glass capable of releasing silver ion is disclosed (see, for example, Patent Document 1).

More concretely, this synthetic resin molded body is constituted by containing, in a synthetic resin, a borosilicate antimicrobial glass containing 0.1 to 20 parts by weight of $Ag_2O$ as monovalent Ag in 100 parts by weight of glass solid formed of one or two or more kinds of network-forming oxides selected from the group consisting of $SiO_2$, $B_2O_3$ and $P_2O_5$ and one or two or more kinds of network-modifying oxides selected from the group consisting of $Na_2O$, $K_2O$, CaO and ZnO. In the example of the patent publication, an antimicrobial glass is disclosed which contains, in a synthetic resin, an antimicrobial glass having an average particle diameter of 20 μm or less formed by adding 2 parts by weight of $Ag_2O$ to 100 parts by weight of a mixture formed of 40 mol % of $SiO_2$, 50 mol % of $B_2O_3$ and 10 mol % of $Na_2O$.

As an antimicrobial resin composition, a resin composition is disclosed which contains a scale-like, antimicrobial glass having a particle diameter of 10 to 1000 μm and a thickness of 0.1 to 20 μm (see, for example, Patent Document 2).

More specifically, the composition of the scale-like glass is composed of 20 to 60% by weight of $SiO_2$, 30 to 70% by weight of $B_2O_3$, 5 to 35% by weight of $Na_2O$ and 0.5 to 3% by weight of $Ag_2O$ when containing $B_2O_3$, and 55 to 80% by weight of $SiO_2$, 0.5 to 30% by weight of $Al_2O_3$, 19.5 to 42% by weight of $Na_2O$ and 0.5 to 3% by weight of $Ag_2O$ when containing no $B_2O_3$.

Moreover, a water-related antimicrobial product is disclosed which contains a silver ion-containing inorganic antimicrobial agent capable of producing an eluted amount of silver ion of 0.5 $ng/cm^2$/day or more when it is immersed in boiling water at 100° C. for 500 to 1,000 hours and subsequently immersed in water or an acid at 20° C. for 24 hours, and an inorganic filler (see, for example, Patent Document 3).

More specifically, a water-related antimicrobial product is disclosed in which a silver ion-containing inorganic antimicrobial agent having an average particle diameter of 2 to 20 μm and containing 0 to 5% by weight of $Ag_2O$ to glass components composing of 56 to 59 mol % of $P_2O_5$, 33 to 38 mol % of MgO+CaO+ZnO and 6 to 8 mol % of $Al_2O_3$ are added in an amount within the range of 0.5 to 5% by weight, and further an inorganic filler is added in an amount within the range of 5 to 80% by weight.

Antimicrobial resin compositions are also proposed in which electric items, such as a dish washer, a dish dryer, a refrigerator, a washing machine and a pot, are provided as examples of the applications of an antimicrobial glass (see, for example, Patent Documents 4 to 6).

According to Patent Documents 4 to 5, that is, antimicrobial resin compositions are proposed which contain, in a molded resin constituting such electric items, an antimicrobial glass having an average particle diameter of 20 μm or less and composing of 40 to 80 mol % of ZnO, 5 to 35 mol % of $SiO_2$ and 5 to 30 mol % of CaO, and an antimicrobial glass having an average particle diameter of 20 μm or less and composing of 54 to 60 mol % of ZnO, 25 to 32 mol % of $B_2O_3$, 7 to 12 mol % of $SiO_2$ and 5 to 8 mol % of alkali metal oxide in predetermined amounts, respectively.

According to Patent Document 6, there is disclosed an antimicrobial glass wherein the maximum diameter (t1) of the antimicrobial glass is adjusted to a value within the range of 1 to 50 mm and the eluted amount of silver ion is adjusted to a value within the range of 0.5 to 100 mg/(g·24 hrs) and a silver ion containing water is prepared by bringing the antimicrobial glass into contact with water directly and a predetermined antimicrobial treatment is applied to a matter to be antibacterialized during or after washing. A method for the production thereof is also disclosed.

Furthermore, as an application of an antimicrobial glass, proposed is a glass water treating agent to be used in water treating apparatuses such as water tanks and cooling towers (see, for example, Patent Document 7).

This is a glass water treating agent which comprises a phosphoric acid-based glass having a maximum diameter of 10 mm or more, wherein the weight composition ratios are $(RO+R_2O)/P_2O_3=0.4$ to 1.2 and $R_2O/(RO+R_2O_3)=0$ to 10 (R is Ca, Na, etc.) and $B/A \geqq 1/3$ where the initial dissolution rate is represented by A and the terminal dissolution rate is represented by B, and the content of metal ion is 0.005 to 5% by weight.

[Patent Document 1] JP1-313531A (Claims)
[Patent Document 2] JP7-25635A (Claims)
[Patent Document 3] JP10-72530A (Claims)
[Patent Document 4] JP2002-3238A (Claims)
[Patent Document 5] JP2002-3239A (Claims)
[Patent Document 6] WO2005/087675 (Claims)
[Patent Document 7] JP7-63701B (Claims)

SUMMARY OF THE INVENTION

However, since the antimicrobial resin compositions disclosed in Patent Documents 1 to 6 are constituted by containing an antimicrobial glass in a resin, the antimicrobial glass is substantially colorless and transparent and silver contained therein often reacts with chloride ion to make the glass discolored or opaque.

Therefore, when using such an antimicrobial resin composition, there has been a problem that even though it is possible to impart a predetermined antimicrobial property to components of electric products, the appearance of the electric products deteriorate greatly during their use.

Patent Document 1, 3 to 5 disclose that the average particle diameter of an antimicrobial glass is preferably 20 μm or less because it is uniformly mixed in a resin. Patent Document 2 discloses that the antimicrobial glass is a scale-like glass having a predetermined size. However, there has been a problem with respect to the production that a classifier, etc. are used together as manufacturing apparatuses and their values should be limited to within predetermined ranges.

With regard to the antimicrobial glass and the glass water treating agent disclosed in Patent Documents 6 and 7, there has been a problem that the maximum diameter is relatively large, but when being used in electric products using water flow such as a dish washer, a dish dryer and a washing machine, they are inferior in discoloration prevention effect or they are easily broken.

Moreover, the antimicrobial glasses disclosed in Patent Documents 1 to 7 are all substantially colorless and transparent. Therefore, there has been a problem that when a covering material is provided to form a cartridge, the presence of an antimicrobial glass can not be recognized from the outside. In other words, there has been a problem that it is difficult to determine a time when the antimicrobial glass needs replenishing or changing when being fabricated into a cartridge and used for an electric product.

The present inventors made researches earnestly and, as a result, found that by adding a predetermined amount of inorganic coloring agent and controlling the size of antimicrobial glass within a predetermined range, it is possible to release a predetermined amount of silver ion repeatedly while maintaining the initial appearance and initial discriminativity even when coming into direct contact with water. Thus, they accomplished the present invention.

That is, an object of the present invention is to provide an antimicrobial glass with which excellent discoloration prevention effect and excellent discriminativity are achieved while the eluted amount of silver ion is maintained within a predetermined range even though an inorganic coloring agent is added, as well as to provide a method for producing an antimicrobial glass.

According to the present invention, there is provided an antimicrobial glass which is a tabular antimicrobial glass capable of exerting an antimicrobial effect by releasing silver ions, wherein the maximum diameter (t1) is adjusted within the range of 3 to 30 mm and which contains an inorganic coloring agent as a compounded component, wherein the addition amount (content) of the inorganic coloring agent is adjusted to a value within the range of 0.001 to 0.5% by weight to the total amount. The aforesaid problems can thereby be solved.

That is, with regard to the antimicrobial glass of the present invention, addition of a predetermined amount of the inorganic coloring agent makes it possible to control the size of the antimicrobial glass and the eluted amount of silver ion to within predetermined ranges and to maintain the initial appearance and initial discriminativity for a long period of time while exerting a predetermined antimicrobial effect. Therefore, it can effectively exert the effect of preventing resin from discoloring due to silver ion by the activity of the inorganic coloring agent, and even when it is provided with a covering material to form a cartridge, it can be recognized from the outside easily, which makes it possible to exactly determine a time when the antimicrobial glass needs replenishing or changing.

If it is an antimicrobial glass having such a large form, it becomes easy to be handled, and by only combining it with a conventional fine particulate antimicrobial glass, the fine antimicrobial glass particles will come into contact with each other and therefore it is possible to effectively prevent aggregation.

In constituting the antimicrobial glass of the present invention, it is preferable that the inorganic coloring agent contain at least one compound selected from the group consisting of cobalt oxide, copper oxide, chromium oxide, nickel oxide, manganese oxide, neodymium oxide, erbium oxide and cerium oxide.

By the use of such a specific compound like cobalt oxide as an inorganic coloring agent, excellent color developability can be caused by its addition even in a relatively small amount and the eluted amount of silver ion is less influenced. As a result, it can exert a predetermined antimicrobial effect and it can maintain its initial appearance and initial discriminativity for a long period of time.

Moreover, particularly by use of cobalt oxide as an inorganic coloring agent, it is possible not only to obtain excellent color developability by addition thereof in an extremely small amount but also to improve and upgrade the shapability and grindability of the antimicrobial glass.

In constituting the antimicrobial glass of the present invention, it is preferable to adjust the ratio expressed by C1/C2 to a value within the range of 0.01 to 3, where the addition amount of the inorganic coloring agent contained in the antimicrobial glass is represented by C1 (% by weight) and the addition amount of silver oxide contained in the antimicrobial glass is represented by C2 (% by weight).

By controlling the addition amount of the inorganic coloring agent in association with the addition amount of silver oxide, it is possible to maintain the initial appearance and initial discriminativity without inhibiting exertion of a predetermined antimicrobial effect.

In constituting the antimicrobial glass of the present invention, it is preferable to adjust the eluted amount of silver ion to a value within the range of 0.01 to 0.45 mg/(g·24 hrs).

If the eluted amount of silver ion is such a value, it is possible to maintain the initial appearance and initial discriminativity for a long period of time while exerting a predetermined antimicrobial effect.

In constituting the antimicrobial glass of the present invention, it is preferable that the antimicrobial glass be chamfered along the edges defining the antimicrobial glass.

By forming such a shape, it is possible to maintain the initial appearance and initial discriminativity for a long period of time while exerting a predetermined antimicrobial effect. Moreover, by forming such a chamfered shape, it is also possible to improve the shapability and grindability of the antimicrobial glass.

Furthermore, if the antimicrobial glass has such a shape, it becomes easy to handle or change it and, even if a relatively strong water flow is used, it is possible to effectively prevent it from flowing away together with the water flow and from being broken.

In constituting the antimicrobial glass of the present invention, it is preferable that the antimicrobial glass contain an antimicrobial glass free from inorganic coloring agents in an amount within the range of 10 to 90% by weight to the total amount.

By adopting such a constitution, it is possible to adjust the eluted amount of silver in the antimicrobial glass and it is also possible to make the discoloration of the antimicrobial glass free from inorganic coloring agent inconspicuous due to the discoloration prevention effect of the antimicrobial glass with a large maximum diameter (t1).

By adoption of such a constitution, even if the antimicrobial glass free from inorganic coloring agent is in the form of fine particles having an average particle diameter as small as 100 μm or less, it is possible to effectively prevent the antimicrobial glass particles from coming into contact with each other to aggregate.

Another aspect of the present invention is a method for producing an antimicrobial glass which is a tabular antimicrobial glass capable of exerting an antimicrobial effect by releasing silver ions, wherein the method has the following steps (A) and (B):

(A) a melting step of heating raw materials to melt them, thereby forming colored molten glass containing an inorganic coloring agent in an amount of 0.001 to 0.5% by weight to the total amount, (B) a molding step of forming an antimicrobial glass having a maximum diameter (t1) of 3 to 30 mm while cooling the colored molten glass.

That is, by use of the method for the production of an antimicrobial glass of the present invention, it is possible to efficiently produce an antimicrobial glass which can maintain its initial appearance and initial discriminativity while exerting a predetermined antimicrobial effect for a long period of time even when it comes into contact with water directly.

In practicing the method for producing an antimicrobial glass of the present invention, step (B) preferably further has a step of grinding an antimicrobial glass.

By use of such a method for producing an antimicrobial glass, it is possible to efficiently produce an antimicrobial glass which can maintain it initial appearance and initial discriminativity for a long period of time while exerting excellent antimicrobial effect since the initial stage.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6(a) to (b) are diagrams for explaining the fabrication of an antimicrobial glass into a cartridge.

FIGS. 7(a) to (c) are diagrams for explaining a covering material of an antimicrobial glass into a cartridge.

FIGS. 9(a) to (b) are diagrams explaining the method for producing an antimicrobial glass (pattern 1).

FIGS. 12(a) to (c) are diagrams explaining the influence of a surface treatment step on the appearance of an antimicrobial glass.

DESCRIPTION OF THE PREFERRED EMBODIMENT

Figure 1:
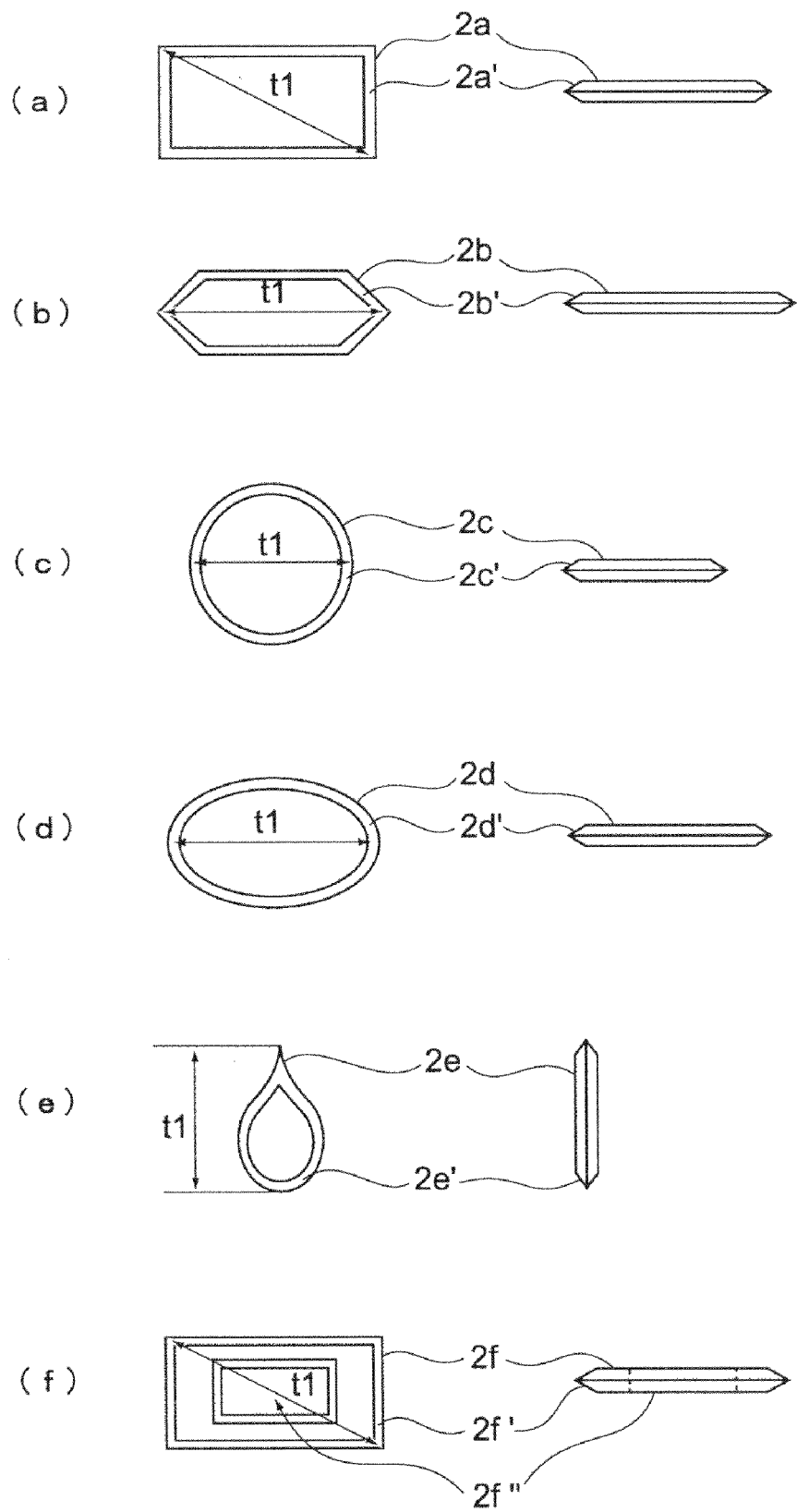
FIGS. 1(a) to (f) are diagrams for explaining the shape of the antimicrobial glass of the first embodiment.

Hereafter, embodiments of the antimicrobial glass of the present invention, the method for producing an antimicrobial glass, and the method for using an antimicrobial glass are explained concretely.

First Embodiment

The first embodiment is an antimicrobial glass which is a tabular antimicrobial glass capable of exerting an antimicrobial effect by releasing silver ions, wherein the maximum diameter (t1) is adjusted within the range of 3 to 30 mm and which contains an inorganic coloring agent as a compounded component, wherein the addition amount of the inorganic coloring agent is adjusted to a value within the range of 0.001 to 0.5% by weight to the total amount.

1. Antimicrobial Glass (1) Shape 1

The antimicrobial glass, which is not particularly restricted with respect to its shape, is preferably a tabular antimicrobial glass 2 (2a to 2f) having a rectangular, polygonal, disc-like, ellipsoidal, deformed or perforated shape as illustrated in FIGS. 1(a) to (f).

A reason for this is that by forming an antimicrobial glass into a tabular shape such as a rectangular shape and a disc-like shape, even when placing it at a predetermined position and bringing into contact with water directly, it is possible to effectively prevent it from washing away from the predetermined position due to water pressure. That is also because if the antimicrobial glass is in a rectangular shape, etc., adjacent antimicrobial glasses are resistant to aggregation during the production or use, and therefore it becomes easier to control the size and shape of the antimicrobial glass during its production and to control the environmental conditions in its use.

It is preferable that the antimicrobial glass be chamfered along the edges defining it as illustrated in FIGS. 1(a) to (f).

A reason for this is that by adopting such a shape, it is possible to maintain the initial appearance and initial discriminativity for a long period of time while exerting a predetermined antimicrobial effect. That is also because by adopting such a chamfered shape, it is possible to improve the shapability and grindability of the antimicrobial glass.

Furthermore, that is also because if the antimicrobial glass has such a shape, it becomes easy to handle or change it and, even if a relatively strong water flow is used, it is possible to effectively prevent it from flowing away together with the water flow and from being broken.

(2) Shape 2

One of the features is that the maximum diameter (t1) of the antimicrobial glass is adjusted to a value within the range of from 3 to 30 mm. The maximum diameter (t1) of an antimicrobial glass means the maximum length of lines optionally drawn in the profile of the antimicrobial glass as illustrated in FIGS. 1(a) to (f).

This is because if the maximum diameter is a value less than 3 mm, it will become easy, when it is placed at a predetermined position and is brought into contact with water directly, to be washed away due to water pressure to flow away from the predetermined position, or it will become difficult to continue to release a predetermined concentration of silver ion for a long period of time, and it may become easy to aggregate during its storage.

That is also because if the maximum diameter exceeds 30 mm, it will become difficult to be handled or it will become difficult to be produced stably.

For such reasons, it is more preferable to adjust the maximum diameter of the antimicrobial glass to a value within the range from 4 to 25 mm, and even more preferably to a value within the range from 5 to 15 mm.

The maximum diameter (t1) of an antimicrobial glass is a maximum diameter in a planar direction when the antimicrobial glass is for example in a tabular shape, and it is the diameter of a sphere when the antimicrobial glass is in a spherical shape.

When the antimicrobial glass is in a tabular shape, it is preferable to adjust the thickness of the antimicrobial glass to a value within the range of 0.1 to 10 mm.

A reason for this is that if the thickness of the antimicrobial glass is a value less than 0.1 mm, it will become difficult to release a predetermined concentration of silver ion, or it will become difficult to be handled, or it will become difficult to be produced stably. That is also because if the thickness of the antimicrobial glass exceeds 10 mm, it will become difficult to be handled or it will become difficult to be produced stably.

For such reasons, it is more preferable, when the antimicrobial glass is in a tabular shape, to adjust the thickness of the antimicrobial glass to a value within the range from 1 to 8 mm, and even more preferably to a value within the range from 2 to 5 mm.

The aforementioned maximum diameter and thickness of an antimicrobial glass can be easily measured using an optical microscope, a vernier caliper, etc.

(3) Shape 3

Next, with regard to the shape of an antimicrobial glass, the relationship between the maximum diameter (t1) of the antimicrobial glass in the planar direction and the residual ratio during the use of the antimicrobial glass is described in detail with reference to FIG. 2. The horizontal axis of FIG. 2 indicates the maximum diameter (mm), in logarithm, of an antimicrobial glass in the planar direction, and the vertical axis indicates the residual ratio (%) measured in accordance with the method for measuring the residual ratio of an antimicrobial glass shown in Examples described below when an antimicrobial glass having the individual particle diameter is used.

Figure 2:
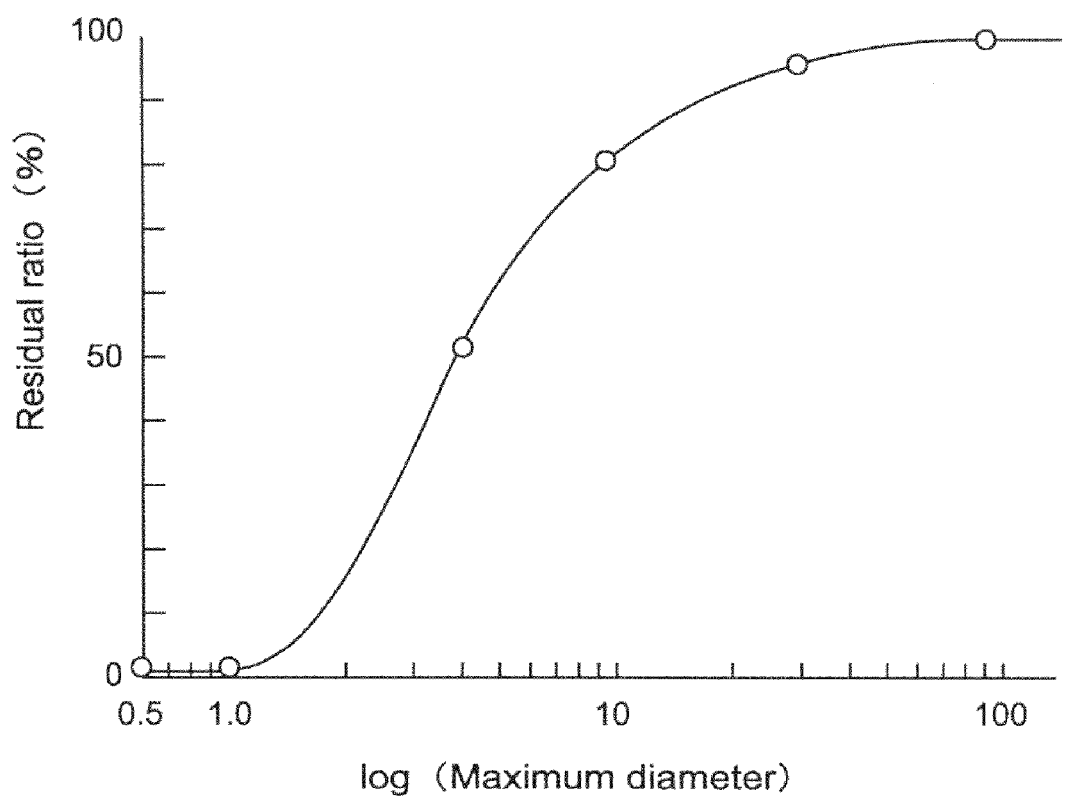
FIG. 2 is a diagram for explaining the relationship between the maximum diameter (t1) of an antimicrobial glass and the residual ratio.

As is clear from FIG. 2, it can be understood that if the maximum diameter (t1) of an antimicrobial glass in the planar direction is a value 5 mm or more, the residual ratio is a relatively high value, i.e., a value 50% or more, and it can withstand a long-term use.

Figure 3:
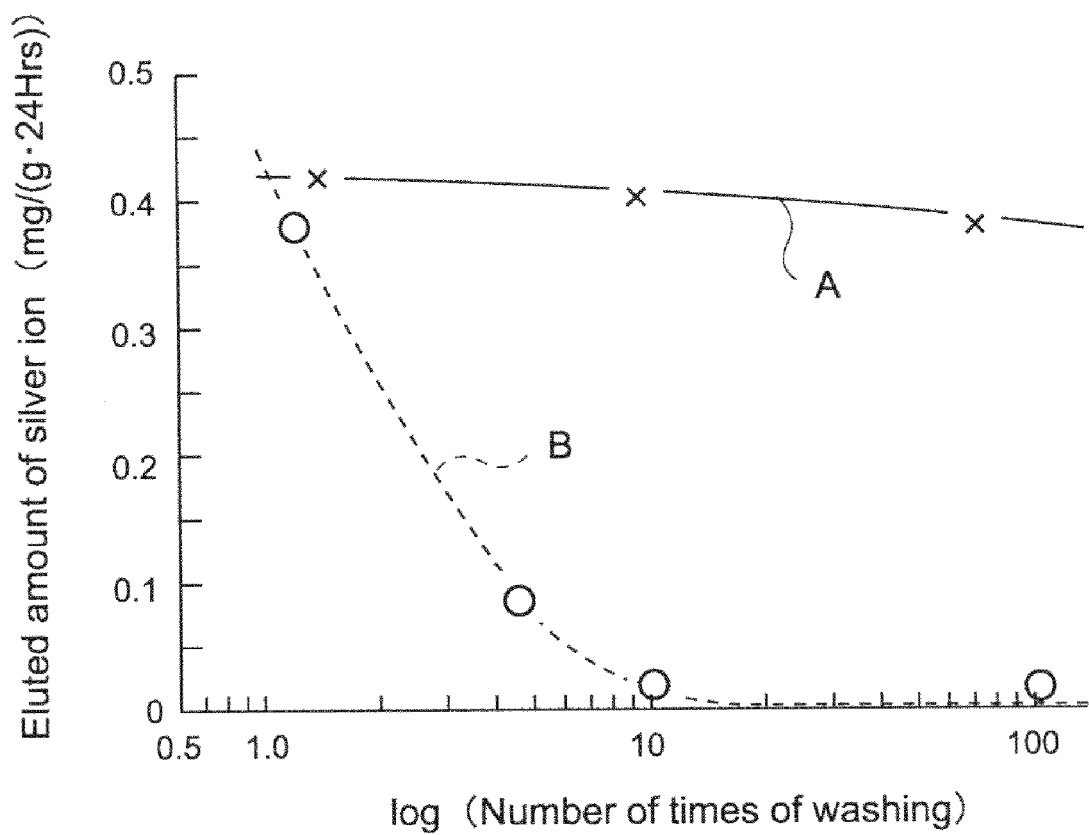
FIG. 3 is a diagram for explaining the relationship between the number of times of washing and the eluted amount of silver ion.

Next, with regard to the shape of an antimicrobial glass, the number of times of washing and the change in the eluted amount of silver ion in a case of using an antimicrobial glass of the present invention (the maximum diameter in the planar direction is 15 mm) and in a case of using an antimicrobial glass having an average particle diameter of 20 μm, respectively, are described in detail with reference to FIG. 3. The horizontal axis of FIG. 3 indicates the number of times of washing using each antimicrobial glass using a washing machine 50 shown in FIG. 8, which is mentioned later, and the vertical axis of FIG. 3 indicates the eluted amount (mg/(g·24 hrs)) of silver ion released into water at each time of washing. In FIG. 3, the data about the antimicrobial glass of the present invention are shown in solid line A, and the data about the antimicrobial glass having an average particle diameter of 20 μm are shown in dotted line B.

As shown in FIG. 3, since the antimicrobial glass of the present invention has a maximum diameter in a planar direction which is a predetermined size and therefore it is not washed away due to water pressure, etc., the residual amount thereof does not decrease greatly. Therefore, it can be understood that it can maintain a desired eluted amount even if it is used repeatedly. Therefore, it can be understood that the antimicrobial glass of the present invention can withstand a long-term use.

On the other hand, since the residual amount of the antimicrobial glass having an average particle diameter of 20 μm decreases every time it is used as shown in FIG. 2, the value of the eluted amount of silver ion decreases greatly in comparison to the eluted amount just after the start of use with increase in the number of times of washing. Therefore, it is understood that it is necessary to refill an antimicrobial glass frequently in order to secure a desired eluted amount of silver ion.

(4) Kind 1

With regard to the kind of the antimicrobial glass, it is preferable to use an antimicrobial glass having the following composition while containing no inorganic coloring agent.

That is, the first glass composition in the antimicrobial glass is preferably configured to contain $Ag_2O$, $ZnO$, $CaO$, $B_2O_3$ and $P_2O_5$, and when the total amount is let be 100% by weight, it is preferable to adjust the content of $Ag_2O$ to a value within the range of 0.2 to 5% by weight, the content of $ZnO$ to a value within the range of 1 to 50%, the content of $CaO$ to a value within the range of 0.1 to 15% by weight, the content of $B_2O_3$ to a value within the range of 0.1 to 15% by weight, the content of $P_2O_5$ to a value within the range of 30 to 80% by weight, and to adjust the weight ratio of $ZnO/CaO$ to a value within the range of 1.1 to 15.

This is because if the weight ratio of $ZnO/CaO$ becomes a value of less than 1.1, it may become difficult to efficiently prevent yellowing of the antimicrobial glass, and if the weight ratio of $ZnO/CaO$ exceeds 15, the antimicrobial glass may suffer from whitening or yellowing.

Accordingly, it is more preferable to adjust the weight ratio expressed by $ZnO/CaO$ to a value within the range of 1.2 to 10, and it is even more preferable to adjust it to a value within the range of 1.5 to 8.

The second glass composition of an antimicrobial glass contains substantially no $ZnO$ and contains $Ag_2O$, $CaO$, $B_2O_3$ and $P_2O_5$. When the total amount is let be 100% by weight, the content of $Ag_2O$ is adjusted to a value within the range of 0.2 to 5% by weight, the content of $CaO$ is adjusted to a value within the range of 15 to 50% by weight, the content of $B_2O_3$ is adjusted to a value within the range of 0.1 to 15% by weight and the content of $P_2O_5$ is adjusted to a value within the range of 30 to 80% by weight. The weight ratio of $CaO/Ag_2O$ is adjusted to a value within the range of 5 to 15.

This is because if the weight ratio of $CaO/Ag_2O$ becomes a value of less than 5, it may become difficult to efficiently prevent yellowing of the antimicrobial glass, and if the weight ratio of $CaO/Ag_2O$ exceeds 15, the antimicrobial glass may suffer from whitening or yellowing.

Accordingly, it is preferable to adjust the weight ratio expressed by $CaO/Ag_2O$ to a value within the range of 6 to 12 and it is more preferable to adjust it to a value within the range of 7 to 10.

The third glass composition of an antimicrobial glass contains $Ag_2O$, $CaO$, $B_2O_3$, $P_2O_5$ and $Al_2O_3$, and when the total amount is let be 100% by weight, the content of $Al_2O_3$ is adjusted to a value within the range of 0.5 to 10% by weight.

This is because addition of $Al_2O_3$ like this can inhibit a deliquescence phenomenon.

In other words, that is because if the content of $Al_2O_3$ becomes less than 0.5% by weight, an effect of inhibiting a deliquescence phenomenon may not be developed. That is also because if the content of $Al_2O_3$ exceeds 10% by weight, an (antimicrobial) effect may not be developed.

It therefore is more preferable to adjust the content of $Al_2O_3$ to a value within the range from 1 to 5% by weight.

(5) Kind 2

Another one of the features is that the antimicrobial glass contains an inorganic coloring agent and that the addition amount of the inorganic coloring agent is adjusted to a value within the range of 0.001 to 0.5% by weight to the total amount.

This is because by adding a predetermined amount of inorganic coloring agent, it is possible to easily limit the size of the antimicrobial glass and the eluted amount of silver ion within predetermined ranges.

Therefore, it is possible to maintain the initial appearance and initial discriminativity for a long period of time while exerting a predetermined antimicrobial effect. In other words, it can effectively exert the effect of preventing resin from discoloring due to silver ion by the activity of the inorganic coloring agent, and even when it is provided with a covering material to form a cartridge, it can be recognized from the outside easily, which makes it possible to exactly determine a time when the antimicrobial glass needs replenishing or changing.

That is also because an antimicrobial glass in such a large size is easy to handle and it is possible to effectively prevent antimicrobial glass fine particles from coming into contact with each other to aggregate just by combining them with conventional antimicrobial glass fine particles.

For such reasons, it is more preferable to adjust the addition amount of the inorganic coloring agent in the antimicrobial glass to a value within the range of 0.003 to 0.1% by weight to the total amount, and it is even more preferable to adjust it to a value within the range of from 0.005 to 0.05% by weight.

Here, the influence of the addition amount of the inorganic coloring agent in an antimicrobial glass is explained with reference to FIGS. 4 and 5.

Figure 4:
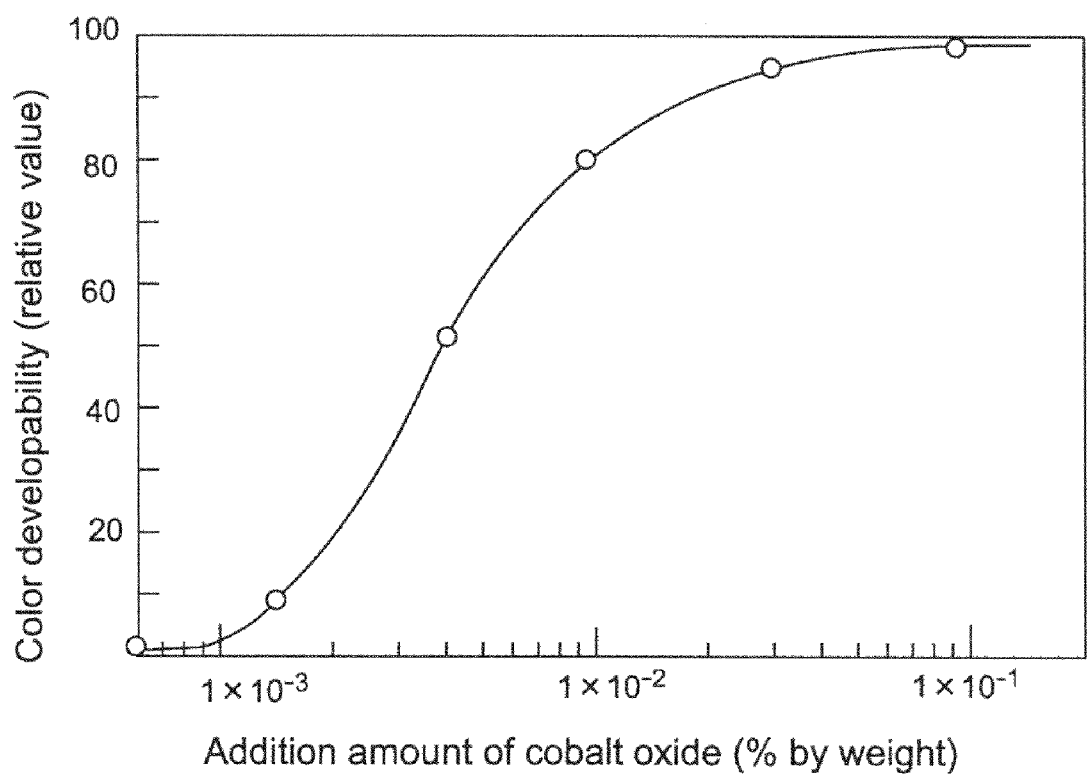
FIG. 4 is a diagram for explaining the relationship between the addition amount of cobalt oxide and the color developability.

The horizontal axis of FIG. 4 indicates the addition amount (% by weight), in logarithm, of cobalt oxide in the antimicrobial glass, and the vertical axis indicates the color developability (relative value) of the antimicrobial glass. With regard to the color developability of an antimicrobial glass, which is a value corresponding to the absorbance of visible light, the larger the number, the better the ability is.

Figure 5:
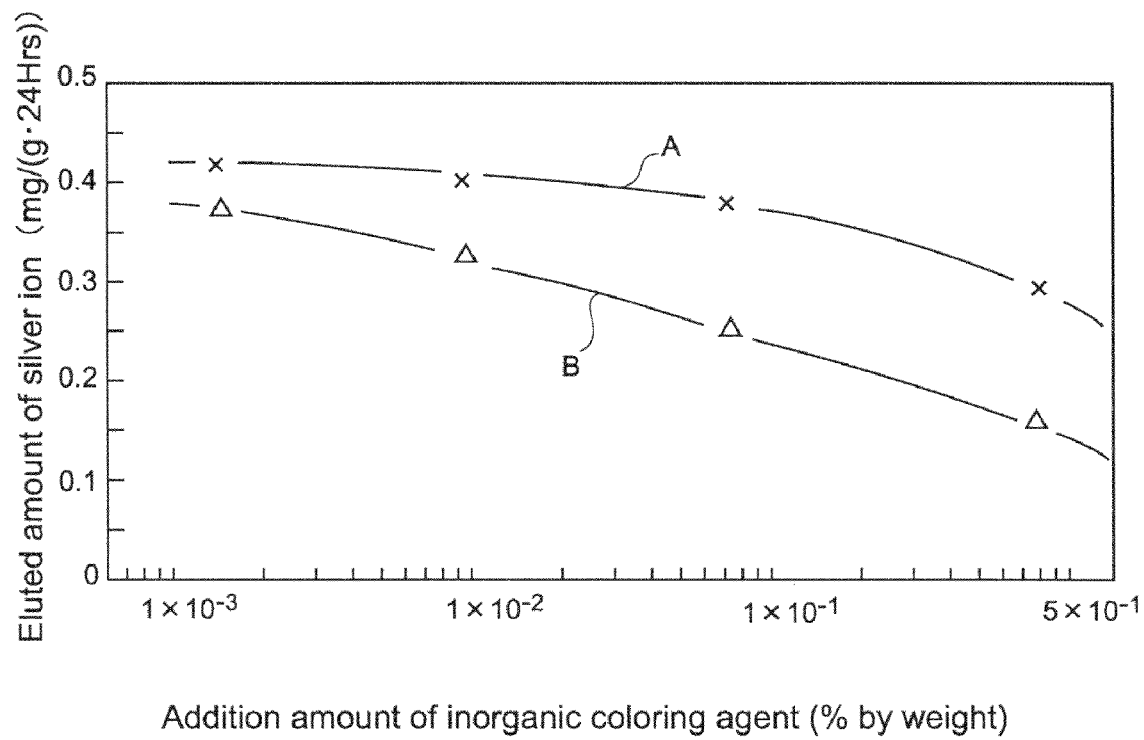
FIG. 5 is a diagram for explaining the relationship between the addition amounts of cobalt oxide and copper oxide and the eluted amount of silver ion.

The horizontal axis of FIG. 5 indicates the addition amount (% by weight), in logarithm, of an inorganic coloring agent (cobalt oxide and copper oxide) in an antimicrobial glass, and the vertical axis indicates the eluted amount (mg/(g·24 hrs)) of silver ion in an antimicrobial glass. In FIG. 5, the characteristic curve with sign A shows a case where cobalt oxide is used as an inorganic coloring agent, and the characteristic curve with sign B shows a case where copper oxide is used as an inorganic coloring agent.

Therefore, as is clear from FIG. 4, when the addition amount of cobalt oxide in an antimicrobial glass is 0.001% by weight or more, a predetermined color developability can be obtained, and as the addition amount of cobalt oxide increases, the color developability is improved, but when the addition amount exceeds 0.1% by weight, the effect tends to saturate.

On the other hand, as is clear from FIG. 5, it is found that the eluted amount of silver ion (mg/(g·24 hrs)) tends to decrease gradually as the addition amount of an inorganic coloring agent (cobalt oxide and copper oxide) in an antimicrobial glass increases.

Therefore, with reference to FIGS. 4 and 5, it can be understood that in order to balance the color developability in the antimicrobial glass and the eluted amount of silver ion, it is effective to adjust the addition amount of an inorganic coloring agent to a value within the range of 0.001 to 0.5% by weight to the total amount.

In considering the addition amount of the inorganic coloring agent contained in an antimicrobial glass, it is preferable to consider the addition amount of silver oxide as well.

That is, it is preferable to adjust the ratio expressed by C1/C2 to a value within the range of 0.01 to 3, where the addition amount of the inorganic coloring agent contained in the antimicrobial glass is represented by C1 and the addition amount of silver oxide contained in the antimicrobial glass is represented by C2.

This is because by controlling the addition amount of the inorganic coloring agent in association with the addition amount of silver oxide, it is possible to maintain the initial appearance and initial discriminativity without inhibiting exertion of a predetermined antimicrobial effect. In other words, that is because if the ratio expressed by C1/C2 becomes less than 0.01, the development of the discoloration prevention effect may become insufficient. That is also because if the ratio expressed by C1/C2 exceeds 3, the development of the antimicrobial effect may become insufficient.

For such reasons, it is more preferable to adjust the ratio expressed by C1/C2 to a value within the range of 0.01 to 2, and it is even more preferable to adjust it to a value within the range of from 0.05 to 1.

(6) Kind 3

The inorganic coloring agent, the kind of which is not particularly restricted, may be only one kind or a combination of two or more kinds selected from among cobalt oxide (CoO), copper oxide (CuO), chromium oxide ($Cr_2O_3$), nickel oxide (NiO), manganese oxide ($MnO_2$), neodymium oxide ($Nd_2O_3$), erbium oxide ($Er_2O_3$) and cerium oxide ($CeO_2$) so that it could develop a color easily in an oxidizing atmosphere.

For example, in the case of cobalt oxide, it is possible to obtain an excellent color developability into a brilliant ink blue color by its addition just in an extremely small amount, for example, as small as 0.005% by weight, and therefore it is possible to maintain the initial appearance and initial discriminativity without inhibiting a predetermined antimicrobial effect.

In the case of copper oxide, it is possible to obtain color developability into sky blue by its addition in a relatively small amount, and therefore it is possible to maintain the initial appearance and initial discriminativity without inhibiting an antimicrobial effect.

In a case of chromium oxide, it is possible to obtain color developability into grass green by addition in a relatively small amount and therefore it is possible to maintain the initial appearance and initial discriminativity.

In a case of nickel oxide, if it contains much potash, it is possible to obtain color developability into dull-green by addition in a relatively small amount and therefore it is possible to maintain the initial appearance and initial discriminativity.

In a case of manganese oxide, if an oxidizing agent is present, it is possible to obtain color developability into brilliant violet by addition in a relatively small amount and therefore it is possible to maintain the initial appearance and initial discriminativity.

In a case of neodymium oxide, it is possible to obtain color developability into lavenderish violet at addition amounts within a wide range even if the addition amount varies, and it is possible to maintain the initial appearance and initial discriminativity. In a case of using a glass raw material containing much iron etc., it is possible to exert its fading effect. In a case of erbium oxide or cerium oxide, it is possible to obtain color developability into a pink color and it is possible to maintain the initial appearance and initial discriminativity.

(7) Eluted Amount of Silver Ion

One feature is that the eluted amount of silver ion in the antimicrobial glass is adjusted to a value within the range of 0.01 to 0.45 mg/(g·24 hrs).

This is because if the eluted amount of silver ion becomes a value less than 0.01 mg/(g·24 hrs), it may become difficult, when bringing it into contact with water directly, to release a predetermined concentration of silver ion quickly to exert a predetermined antimicrobial effect.

That is also because that if the eluted amount of silver ion exceeds 0.45 mg/(g·24 hrs), it may become difficult to continue to release a predetermined concentration of silver ion for a long period of time or it may become difficult to be handled or it may become difficult to be produced stably.

For such reasons, it is preferable to adjust the eluted amount of silver ion in the antimicrobial glass to a value within the range of 0.01 to 0.40 mg/(g·24 hrs), and it is more preferable to adjust it to a value within the range of 0.02 to 0.35 mg/(g·24 hrs).

The eluted amount of silver ion in an antimicrobial glass can be measured in accordance with the measuring method disclosed in Example 1 shown below. Conventionally, it has been believed that in use in a washing machine, etc., the eluted amount of silver ion in an antimicrobial glass is preferably a value within the range of 0.5 to 100 mg/(g·24 hrs). However, it has been found that since the antimicrobial effect is increased through repetition of washing, a comparable level of antimicrobial effect can be obtained even at a smaller eluted amount of silver ion.

2. Covering Material or Additives (1) Complexing Compound

It is preferable to add singly or in combination of two or more kinds of complexing compound capable of forming a complex together with a silver ion, such as ammonium sulfate, ammonium nitrate, ammonium chloride, sodium thiosulfate, ammonium sulfide, ethylenediaminetetraacetic acid (EDTA), ammonium acetate, ammonium perchlorate, and ammonium phosphate.

The reason for this is that addition of such a complexing compound makes it possible to prevent the antimicrobial glass from discoloring or coloring remarkably well.

Since it is possible to form a complex easily together with a silver ion to prevent coloring even if the atmosphere is strongly alkalic, for example, the pH value is 10 or more, it is more preferable to use at least one compound selected from the group consisting of ammonium sulfate, ammonium nitrate, ammonium chloride and sodium thiosulfate as a complexing compound.

It is preferable to adjust the addition amount of the complexing compound to a value within a range of 0.01 to 30% by weight to the total amount.

A reason for this is that if the addition amount of the complexing compound is less than 0.01% by weight, it may become difficult to prevent discoloration effectively. That is also because if the addition amount of the complexing compound exceeds 30% by weight, the antimicrobial properties of the antimicrobial glass may deteriorate or it may become difficult to achieve uniform mixing.

Accordingly, it is preferable to adjust the addition amount of the complexing compound to a value within a range of 0.1 to 20% by weight, more preferably a value within a range of 0.5 to 10% by weight to the total amount because the balance between the discoloration resistance and the antimicrobial property, etc. in the antimicrobial glass is good.

(2) Covering Material

It is also preferable to produce a form in which the antimicrobial glass is covered with an inorganic substance and an organic substance as a covering material.

The reason for this is that such a constitution can make it easy to control the elution rate of silver ion and can improve the antiaggregating property of the antimicrobial glass.

As the particles which cover the antimicrobial glass, preferred is used singly or in combination of two or more kinds selected from among titanium oxide, silicon oxide, colloidal silica, zinc oxide, tin oxide, lead oxide, white carbon, acrylic particles, styrene particles, polycarbonate particles, etc.

Further, while the method for covering an antimicrobial glass with particles is not specifically restricted, it is preferable, for example, to mix the particles with the antimicrobial glass uniformly, followed by welding them to the glass by heating at a temperature of 600 to 1200° C., or to fix the particles to the glass with a bonding agent.

It is preferable to form a cartridge by providing a packaging material 18' as a covering material or providing a housing around an antimicrobial glass 10' as shown in FIGS. 6(*a*) and (*b*).

This is because provision of such a covering material will increase easiness in handling during storage or can prevent the antimicrobial glass from aggregation. That is also because the usability is improved in use and when using relatively strong water flow, it is possible to prevent it from flowing away from a predetermined position. Another reason is that since a cartridge has been formed, it is possible to perform handling or changing easily.

It is also preferable to package a plurality of antimicrobial glass 10 using a moisture-proof material such as an aluminum laminate film 16 as illustrated in FIG. 7(*a*), or to package them separatingly as illustrated in FIG. 7(*b*), or to cover them with a material 18 with holes as illustrated in FIG. 7(*c*).

(3) Surface Treatment

For the purpose of preventing oxidation or coloring, it is preferable to add a surfactant, stearic acid, myristic acid, sodium stearate, or a silane coupling agent as a dispersing agent, or a hindered phenol compound, a hindered amine compound as an antioxidant, or a pigment or a dye as a coloring agent, to an antimicrobial glass.

While it is preferable to determine the addition amount of such an additive in consideration of the addition effect etc., it is more preferable to adjust each amount, for example, to a value within the range of 0.01 to 30% by weight to the total amount.

3. Usage Example 1

In using the antimicrobial glass of the present invention, it is preferable to add an antimicrobial glass free from inorganic coloring agents to the antimicrobial glass in an amount within the range of 10 to 90% by weight to the total amount.

The reason for this is that by adopting such a constitution, it is possible to adjust the eluted amount of silver in the antimicrobial glass and it is also possible to make the discoloration of the antimicrobial glass free from inorganic coloring agent inconspicuous due to the discoloration prevention effect of the antimicrobial glass with a large maximum diameter (t1).

By adoption of such a constitution, even if the antimicrobial glass free from inorganic coloring agent is in the form of fine particles having an average particle diameter as small as 100 μm or less, the antimicrobial glass containing an inorganic coloring agent can effectively prevent the antimicrobial glass particles free from inorganic coloring agent from coming into contact with each other to aggregate.

For such reasons, it is more preferable to add the antimicrobial glass free from inorganic coloring agent in an amount within the range of 20 to 80% by weight to the total amount, and it is even more preferable to add it in an amount within the range of from 30 to 70% by weight.

4. Usage Example 2

In using the antimicrobial glass of the present invention, it is preferable to contain the following steps (C) to (D):

(C) a step of bringing the antimicrobial glass into contact with water directly to produce water containing silver ion (this step may be called a contacting step), (D) a step of treating a matter to be antibacterialized with the water containing silver ion to subject it to an antimicrobial treatment (this step may be called an antimicrobial step).

Figure 8:
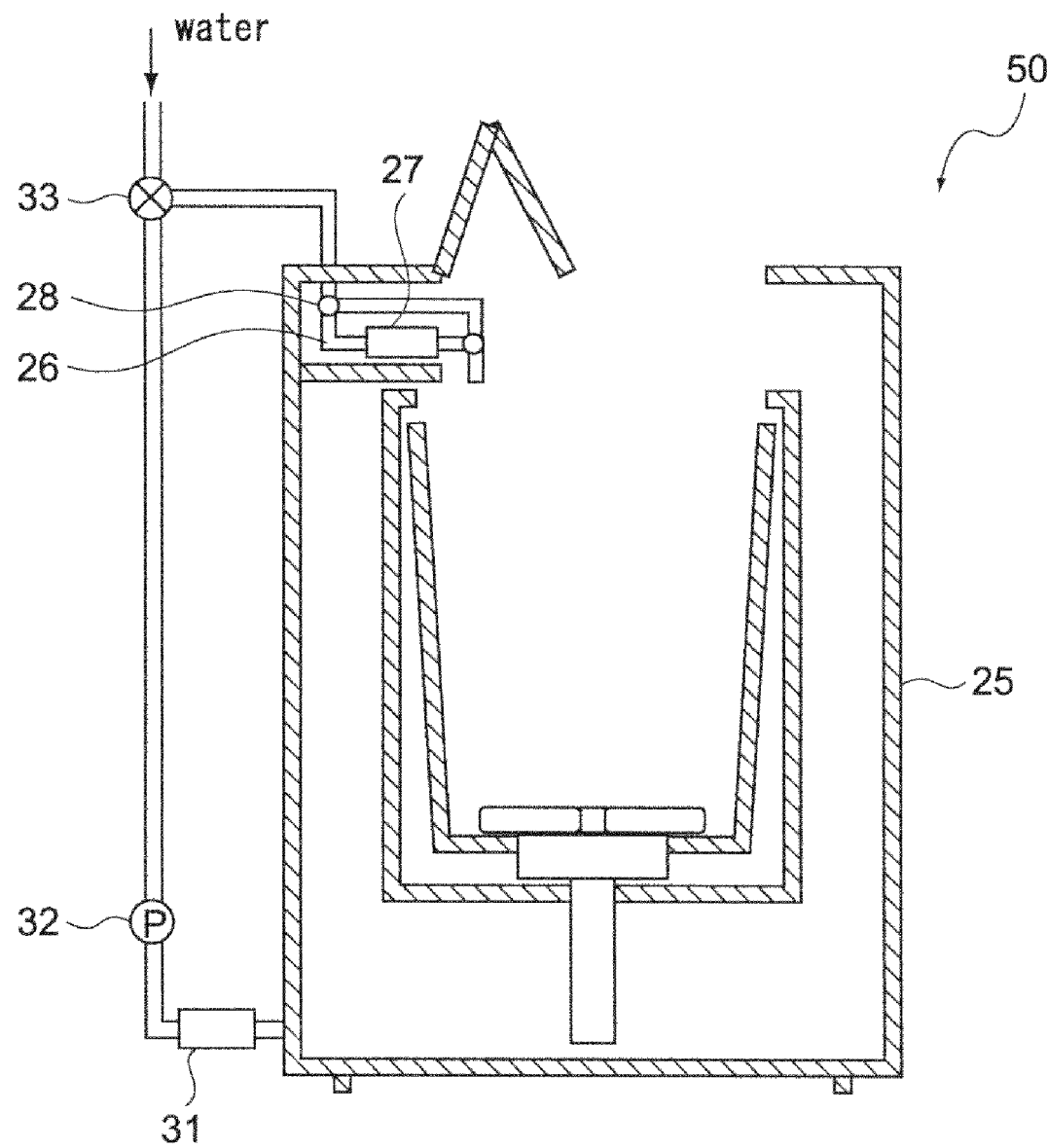
FIG. 8 shows one example of a washing machine to which an antimicrobial glass is applied.

Assuming a case of using it in a washing machine 50 shown in FIG. 8, the method of using the antimicrobial glass is hereafter described concretely. For making the explanation easy, a unit for recycling washing water is drawn outside a washing bath 25 in FIG. 8, but it is usually provided inside the washing bath 25.

(1) Contacting Step

While the method for bringing an antimicrobial glass into contact with water directly is not particularly restricted, it is preferable to bring the antimicrobial glass into contact with the water directly, for example, by immersing the antimicrobial glass into water or by charging the antimicrobial glass into water flow, thereby producing water containing silver ion.

In this step, if the antimicrobial glass is used for example in a washing machine, it is preferable that a bypass 26 be provided and an antimicrobial glass 27, which has been fabricated into a cartridge, be put on the bypass as illustrated in the upper portion of FIG. 8, and a valve 28 leading to the bypass 26 be opened or closed at a necessary time, thereby causing water to flow in and bring it into contact with the antimicrobial glass 27 directly to obtain water containing silver ion.

The reason for this is that by using water containing silver ion only in the final stage of washing, it is possible to prevent silver ion from flowing away to waste, in other words, it is possible to effectively limit the used amount of the antimicrobial glass when an antimicrobial treatment is applied to a matter to be washed.

On the other hand, it is preferable that when used water is recycled, lint and the like be treated through a filter as illustrated in the lower portion of FIG. 8, and at the same time the water be brought into contact with the antimicrobial glass 31. In other words, it is preferable to reuse antimicrobial treated water via a pump 32 and a valve 33.

(2) Antimicrobial Step

It is also preferable to perform an antimicrobial treatment by treating a matter to be antibacterialized by showering water containing silver ion to the matter or immersing the matter directly into the water.

Typical examples of the matter to be antibacterialized in the case of washing machines include woven fabrics, fibers, nonwoven fabrics, mat-like materials, clothes, towels, footwear and underwears.

Second Embodiment

The second embodiment is a method for producing an antimicrobial glass which is a tabular antimicrobial glass capable of exerting an antimicrobial effect by releasing silver ions, wherein the method has the following steps (A) and (B):

(A) a melting step of heating raw materials to melt them, thereby forming colored molten glass containing an inorganic coloring agent in an amount of 0.001 to 0.5% by weight to the total amount, (B) a molding step of forming an antimicrobial glass having a maximum diameter (t1) of 3 to 30 mm while cooling the colored molten glass.

That is, by use of the method for the production of an antimicrobial glass of the present invention, it is possible to efficiently produce an antimicrobial glass which can maintain its initial appearance and initial discriminativity while exerting a predetermined antimicrobial effect for a long period of time even when it comes into contact with water directly.

1. Melting Step

Raw materials are agitated until they are mixed uniformly by use of a universal mixer at a rotational speed of 250 rpm for 30 minutes so that the aforementioned first glass composition or the second glass composition could be produced. At this time, an inorganic coloring agent such as cobalt oxide is added so as to achieve a value within the range of 0.001 to 0.05% by weight.

Subsequently, a glass melt is produced by heating the glass raw materials using a melting furnace under a condition characterized, for example, by at 1280° C. and for 3.5 hr.

The heating condition in the melting furnace may be appropriately changed depending upon the kinds and compounding ratios of the raw materials.

2. Molding Step

The molding step is a step of processing a molten glass obtained by melting glass raw materials into an antimicrobial glass having a predetermined shape.

Concretely, as shown in FIGS. 9(*a*) to (*b*), it is possible to perform chocolate cutting utilizing so-called thin-wall portions by production using predetermined rotating members 20*a*, 20*b*. It is possible to efficiently obtain an antimicrobial glass 10 which is easy to handle or the surface area and shape of which can be adjusted easily.

That is, it is possible to form an antimicrobial glass 10 having a predetermined shape by causing molten glass 22 to freely fall from above to between a pair of rotating members 20*a* and 20*b* and utilizing recessed portions 24 formed in the surface of the rotating member 20*a*. It is preferable that cooling pipes (not shown) be provided in the central portions of the pair of rotating members 20*a* and 20*b* and the rotating members 20*a* and 20*b* be configured so that their surface temperature could be controlled. Moreover, since the antimicrobial glass has been shaped in a strip-like form via the thin-wall portions and therefore a predetermined temperature is maintained, it is preferable to blow cooling wind to the surface of the antimicrobial glass when it is desired to be further cooled.

Figure 10:
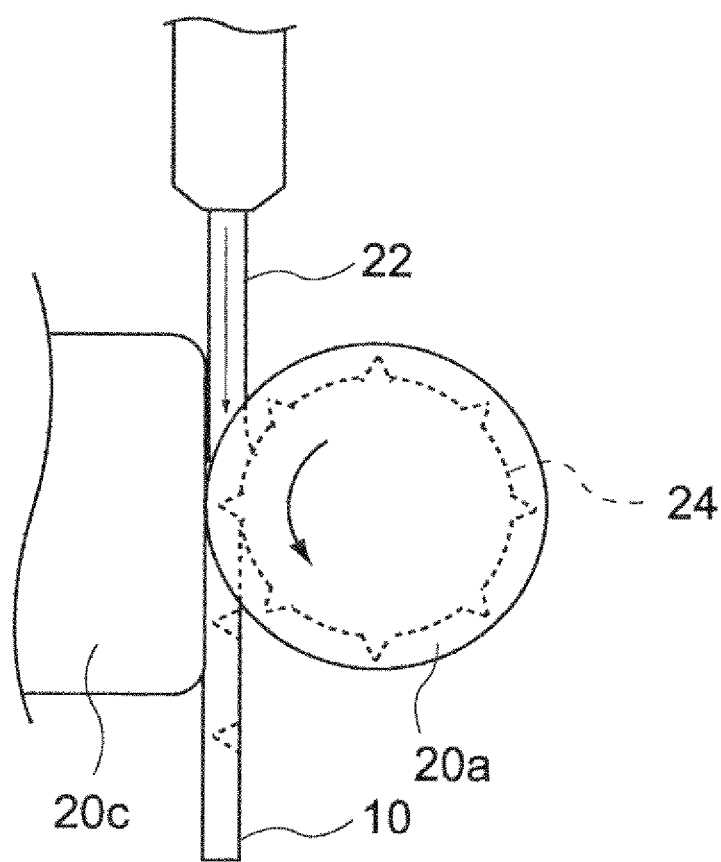
FIG. 10 is a diagram for explaining another method for producing an antimicrobial glass.

While the molding machine illustrated in FIGS. 9(*a*) and (*b*) has a pair of rotating members 20*a* and 20*b*, it is possible, as a modification example, to obtain a tabular antimicrobial glass 10 having a shape substantially the same by using a flat wall member 20*c* as illustrated in FIG. 10 instead of one rotating member 20*b*.

3. Surface Grinding Step

It is preferable to secure a clean surface through removal of foreign matters or the like attached to the surface of an antimicrobial glass and to remove flashes and further to chamfer the tabular antimicrobial glass along its edges by mixing and agitating the resulting tabular antimicrobial glass together with water or alcohol (e.g., isopropyl alcohol) at room temperature for about 10 min to 24 hrs using an agitating machine or a pulverizing machine such as a V blender, a ball mill and a vibration ball mill.

This is because by performing such a surface grinding step, the eluted amount of silver will increase since the initial stage and therefore it will also become easy to control the eluted amount of silver.

For example, when a surface grinding step (room temperature, 30 min) using water or isopropyl alcohol is applied in a vibration ball mill to the antimicrobial glass obtained in Example 1, it has been confirmed that the eluted amount of silver is 0.45 mg/(g·24 hrs) and that the eluted amount of silver decreases to about ⅓, that is, 0.16 mg/(g·24 hrs) when such a surface grinding step is omitted.

EXAMPLES

The present invention is further explained in detail based on examples hereinafter. However, the explanation described hereinafter is made only for an illustration purpose and the present invention is not limited by the description.

Example 1

1. Preparation of Antimicrobial Glass
(1) Melting Step

As the first glass composition as shown in Table 1, glass raw materials corresponding to the glass composition were agitated at a rotation speed of 250 rpm for 30 minutes using a universal mixer until they were mixed uniformly so that the content of $Ag_2O$ might have become 3% by weight, the content of ZnO might have become 30% by weight, the content of CaO might have become 20% by weight, the content of $B_2O_3$ might have become 5% by weight, the content of $P_2O_5$ might have become 42% by weight, and the content of CoO as a coloring agent might have become 0.01% by weight, where the total amount is 100%.

Subsequently, a molten glass was prepared by heating the glass raw materials using a glass melting furnace under a condition characterized by at 1280° C. and for 3.5 hr.

(2) Molding Step

The molten glass taken out from the glass melting furnace was introduced into a molding machine 40 like that shown in FIG. 9, thereby forming a disc-shaped antimicrobial glass (rectangular piece, maximum diameter (t1): 15 mm, thickness (t2): 4 mm).

(3) Surface Grinding Step

The resulting tabular antimicrobial glass 500 g was charged into a vibration ball mill using no media. Subsequently, 500 g of isopropyl alcohol or water was added, and in this state the vibration ball mill was worked under a condition characterized by at room temperature and for 30 minutes to perform a surface grinding step containing a flash removing step.

As a result, while minute irregularities had been found before the surface grinding step as shown in FIG. 12(*a*), the surface was smoothened and emitted gloss after the surface grinding step as shown in FIG. 12(*b*).

2. Evaluation of Antimicrobial Glass
(1) Evaluation of Silver Ion Elution Property 10 g of the obtained antimicrobial glass was immersed in 100 ml of distilled water (20° C.) and was subjected to shaking for 24 hour using a shaker. After separating a silver ion elute using a centrifugal separator, it was filtered with a filter paper (5C) to produce a measuring sample. Subsequently, silver ion in the measuring sample was measured by ICP emission spectrophotometry method and the eluted amount of silver ion (mg/g·24 hrs) in the antimicrobial glass was calculated.

(2) Evaluation of Flowability

A recessed portion having a depth of 0.5 mm and an area of 5 cm×5 cm was formed on the surface of a stainless plate having a thickness of 1 mm and an area of 20 cm×20 cm, and then while 100 g (W1) of antimicrobial glass was filled therein, tap water at a flow rate of 1 liter/min was sprayed from the lateral direction. After continuing this state for 1 min, the weight (W2) of the antimicrobial glass remaining on the stainless plate was measured, and the residual ratio of the antimicrobial glass ((W1−W2)/W1×100) was calculated. Then, the flowability of the antimicrobial glass was evaluated from the calculated residual ratio in accordance with the following criteria.

Very Good: The residual ratio is 90 to 100% by weight.
Good: The residual ratio is 70 to less than 90% by weight.
Fair: The residual ratio is 30 to less than 70% by weight.
Bad: The residual ratio is less than 30% by weight.

(3) Evaluation of Antimicrobial Property

The evaluation of the antimicrobial property to cotton cloth by the resulting antimicrobial glass was performed using a washing machine. That is, 3 kg of cotton cloth was washed by use of a washing machine shown in FIG. 8 while circulating tap water containing detergent.

After completion of the washing, a valve leading to a bypass on which an antimicrobial glass packaged in a cartridge was placed was opened and closed to allow water to flow, thereby bringing the antimicrobial glass into contact with water directly to produce silver ion containing water. Moreover, water which was appropriately subjected to antimicrobial treatment using an antimicrobial glass was recycled. Then, the antimicrobial treated water was supplied to cotton cloth as a matter to be antibacterialized, and thereby an antimicrobial treatment was performed.

The obtained cotton cloth was thus left at rest under an environment at 35° C., 95% Rh for 48 hr and then its antimicrobial property was evaluated under the following conditions.

Very Good: Neither generation of smell nor generation of darkening was observed.
Good: Almost no generation of smell and almost no generation of darkening were observed.
Fair: Some generation of smell or some generation of darkening was observed.
Bad: Remarkable generation of smell or generation of darkening was observed.

(4) Discoloration Prevention Effect

Figure 11:
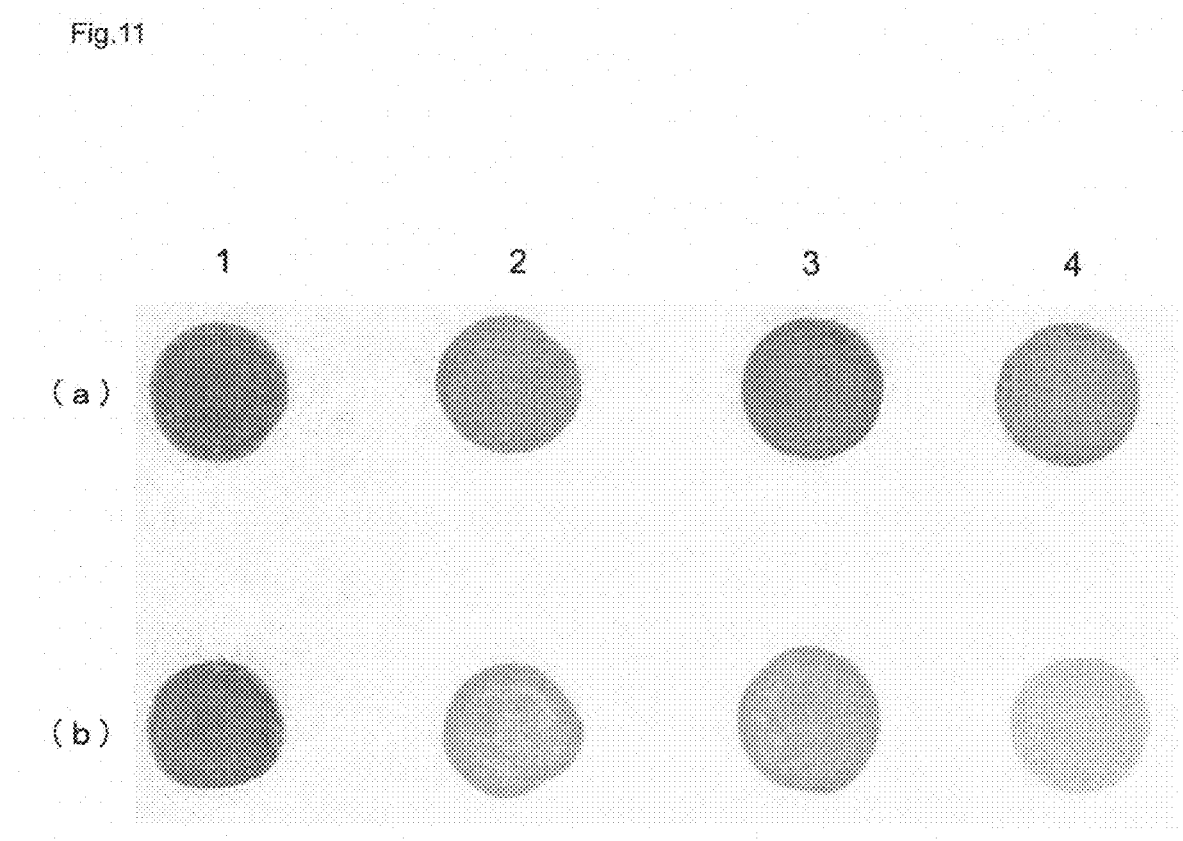
FIGS. 11(a) to (b) are diagrams explaining the discoloration prevention effect of an antimicrobial glass.

The antimicrobial property evaluation was performed as described above by using a washing machine, and the discoloration prevention effect of the resulting antimicrobial glass was evaluated. That is, after performing the antimicrobial property evaluation for 48 hours using the washing machine shown in FIG. 8, the antimicrobial glass was taken out and then the discoloration prevention effect was evaluated under the following conditions. In FIG. 11(*a*), photographs of the antimicrobial glass before the start of the evaluation and after the completion of the evaluation are shown.

Very Good: No discoloration and the like are observed in the antimicrobial glass.
Good: Almost no discoloration and the like are observed in the antimicrobial glass.
Fair: A slight discoloration and the like are observed in the antimicrobial glass.
Bad: A remarkable discoloration and the like of the antimicrobial glass are observed.

(5) Evaluation of Discriminativity

The antimicrobial property evaluation was performed as described above by using a washing machine, and the discoloration prevention effect of the resulting antimicrobial glass was evaluated. That is, after performing the antimicrobial property evaluation for 48 hours using the washing machine shown in FIG. 8, the antimicrobial glass packaged in a cartridge was taken out and then the discriminativity was evaluated under the following conditions as shown in FIG. 7(*c*).

Very Good: The presence of the antimicrobial glass in a cartridge can be recognized clearly.
Good: The presence of the antimicrobial glass in a cartridge can be recognized easily.
Fair: The presence of some part of the antimicrobial glass in a cartridge can not be recognized.

Bad: The presence of the antimicrobial glass in a cartridge can not be recognized at all.

Examples 2 to 5

In each of Examples 2 to 5, an antimicrobial glass was produced and evaluated in the same manner as Example 1 except for changing the composition ratios of the glass and the inorganic coloring agent (cobalt oxide) used in Example 1 as shown in Table 1.

Comparative Examples 1 to 3

In Comparative Example 1, evaluation was performed in the same manner as Example 1 except for changing the addition amount of cobalt oxide in Example 1 to 0.0001% by weight.

In Comparative Example 2, evaluation was performed in the same manner as Example 1 except for adding iron oxide ($Fe_2O_3$) in place of cobalt oxide (CoO) in Example 1 and adjusting the addition amount thereof to 0.0001% by weight.

Further, in Comparative Example 3, evaluation was performed in the same manner as Example 1 except for changing the addition amount of cobalt oxide in Example 1 to 0% by weight, that is, adding no cobalt oxide.

In FIGS. 11(a) to (b), photographs of the antimicrobial glasses before the start of the evaluation of the discoloration prevention effect in Comparative Examples 1 to 3 and after the completion of the evaluation are shown.

mum diameter (t1) within a predetermined range and containing a predetermined amount of inorganic coloring agent as a compounded component.

Therefore, by treating a matter to be antibacterialized with a silver ion containing water obtained by directly contacting water and an antimicrobial glass having a maximum diameter (t1) within a predetermined range and containing a predetermined amount of inorganic coloring agent, it is possible, for example, to release a predetermined amount of silver ion rapidly and to efficiently perform a predetermined antimicrobial treatment to the matter to be antibacterialized during washing, and it is also possible to exert a similar antimicrobial effect for the matter to be antibacterialized which was washed repeatedly.

Therefore, the antimicrobial glass of the present invention can be used suitably for various apparatus, such as a washing machine, a dish washer, an iron, a humidifier, a food washing tank, an instrument washer for medical applications, a water tank for a flush toilet, a machine for washing cattle sheds, a rotary washing machine for artificial lawn grounds, a water circulation machine for bathtubs, a cooling tower for air conditioning, a spray pump, and a hose for horticulture.

In particular, even in an iron and a washing machine or a dish washer to which considerable vibrations are applied, the antimicrobial glass of the present invention can exhibit excellent mechanical properties and durability and is not darkened in its appearance. Therefore, there are suitable applications for the antimicrobial glass of the present invention.

TABLE 1

| | | Example 1 | Example 2 | Example 3 | Example 4 | Example 5 | Comparative Example 1 | Comparative Example 2 | Comparative Example 3 |
|---|---|---|---|---|---|---|---|---|---|
| Glass composition | $P_2O_5$ | 42 | 62 | 37 | 37 | 57 | 32 | 52 | 32 |
| | ZnO | 30 | — | 30 | 30 | — | 30 | — | 30 |
| | $SiO_2$ | 5 | 5 | 5 | 5 | 10 | 5 | 5 | 5 |
| | CaO | 20 | 30 | 25 | 25 | 30 | 30 | 35 | 30 |
| | $Ag_2O$ | 3 | 3 | 3 | 3 | 3 | 3 | 3 | 3 |
| | Coloring agent | CoO 0.01 | CoO 0.03 | CoO 0.05 | CoO 0.008 | CoO 0.002 | CoO 0.0001 | Fe2O3 0.0001 | 0 |
| | Shape | Disk | Disk | Disk | Disk | Disk | Disk | Disk | Disk |
| | Maximum diameter(t1) (mm) | 12 | 12 | 15 | 20 | 25 | 12 | 12 | 12 |
| | Thickness (t2) (mm) | 4.0 | 4.0 | 2.0 | 5.0 | 8.0 | 4.0 | 4.0 | 4.0 |
| | Eluted amount (mg/g/24 Hr) | 0.30 | 0.35 | 0.10 | 0.10 | 0.15 | 0.02 | 0.01 | 0.02 |
| | Flowability | Very Good | Very Good | Very Good | Very Good | Very Good | Bad | Bad | Bad |
| | Antimicrobial property | Very Good | Very Good | Good | Good | Good | Bad | Fair | Bad |
| | Discoloration prevention effect | Very Good | Very Good | Very Good | Good | Fair | Bad | Good | Bad |
| | Discriminativity | Very Good | Very Good | Good | Good | Fair | Bad | Fair | Bad |

INDUSTRIAL APPLICABILITY

According to the antimicrobial glass of the present invention, by limiting the maximum diameter (t1) to within a predetermined range and by containing a predetermined amount of inorganic coloring agent as a compounded component, it has become possible to release a predetermined amount of silver ion repeatedly while maintaining the initial appearance and initial discriminativity even if coming into contact with water directly.

According to the method for producing an antimicrobial glass of the present invention, it has become possible to efficiently obtain such an antimicrobial glass having a maxi-

What is claimed is:

1. An antimicrobial glass comprising:
   a tabular antimicrobial glass comprising a glass composition and silver oxide capable of exerting an antimicrobial effect by releasing silver ions from the silver oxide, wherein the maximum diameter (t1) of the antimicrobial glass is adjusted within a range of 3 to 30 mm and,
   an inorganic coloring agent as a compounded component, wherein an addition amount of the inorganic coloring agent is adjusted to a value within the range of 0.001 to 0.5% by weight relative to a total amount of the antimicrobial glass,
   wherein the inorganic coloring agent is cobalt oxide, wherein an amount of the silver ions eluted from the silver oxide is adjusted to a value within a range of 0.01 to 0.45 mg/(g·24 hrs), and wherein a ratio expressed by C1/C2 is in a range of 0.0006 to 3, where C1 is an amount of the inorganic coloring agent and C2 is an amount of the silver oxide relative to the total amount of the antimicrobial glass.

2. The antimicrobial glass according to claim 1, wherein the antimicrobial glass is chamfered along the edges defining the antimicrobial glass.

3. A method for producing an antimicrobial glass, the method comprising:

heating raw materials including an inorganic coloring agent and silver oxide for releasing silver ions to exert an antimicrobial effect to melt the raw materials, thereby forming a colored molten glass, wherein the inorganic coloring agent is cobalt oxide, and an amount of the inorganic coloring agent is 0.001 to 0.5% by weight relative to a total amount of the raw materials, and forming an antimicrobial glass having a maximum diameter (t1) of 3 to 30 mm while cooling the colored molten glass such that an amount of the silver ions eluted from the silver oxide is adjusted to a value within a range of 0.01 to 0.45 mg/(g·24 hrs)

wherein a ratio expressed by C1/C2 is in a range of 0.0006 to 3, where C1 is an amount of the inorganic coloring agent and C2 is an amount of the silver oxide relative to the total amount of the antimicrobial glass.

4. The method for producing an antimicrobial glass according to claim 3, further comprising grinding the antimicrobial glass in the forming of the antimicrobial glass.

* * * * *